United States Patent [19]

Mercer et al.

[11] 4,169,314

[45] Oct. 2, 1979

[54] DENTAL ARTICULATOR FOR MOUNTING CASTS WITHOUT PLASTER

[76] Inventors: Roger W. Mercer, 1340 Arlington Dr., Fairborn, Ohio 45324; Louis E. Hay, 847 Woodhill Rd., Dayton, Ohio 45431

[21] Appl. No.: 837,002

[22] Filed: Sep. 27, 1977

[51] Int. Cl.[2] ............................................. A61C 11/00
[52] U.S. Cl. ............................................................ 32/32
[58] Field of Search ............................................. 32/32

[56] References Cited

U.S. PATENT DOCUMENTS

| | | | |
|---|---|---|---|
| 537,812 | 4/1895 | Bragg | 32/32 |
| 1,553,492 | 9/1925 | Williams | 32/32 |
| 2,535,146 | 12/1950 | Lyons | 32/32 |
| 2,613,440 | 10/1952 | Murray et al. | 32/32 |
| 2,621,407 | 12/1952 | Schlesinger | 32/32 |
| 2,700,219 | 1/1955 | Lindley | 32/32 |
| 3,224,095 | 12/1965 | Turner | 32/32 |

*Primary Examiner*—Russell R. Kinsey
*Assistant Examiner*—John J. Wilson

[57] ABSTRACT

A dental articulator for mounting stone dental casts by means of a screw engaging a threaded aperture in the base of the dental casts in lieu of the prior method of mounting the casts by means of plaster. The threaded apertures may be formed directly into the casts, or by the preferred method of embedding plastic threaded buttons into the stone casts. This mounting method permits a more rapid mounting of the dental casts in the articulator and also permits a very rapid removal and remounting of the casts to their precise prior occlusion position.

20 Claims, 9 Drawing Figures

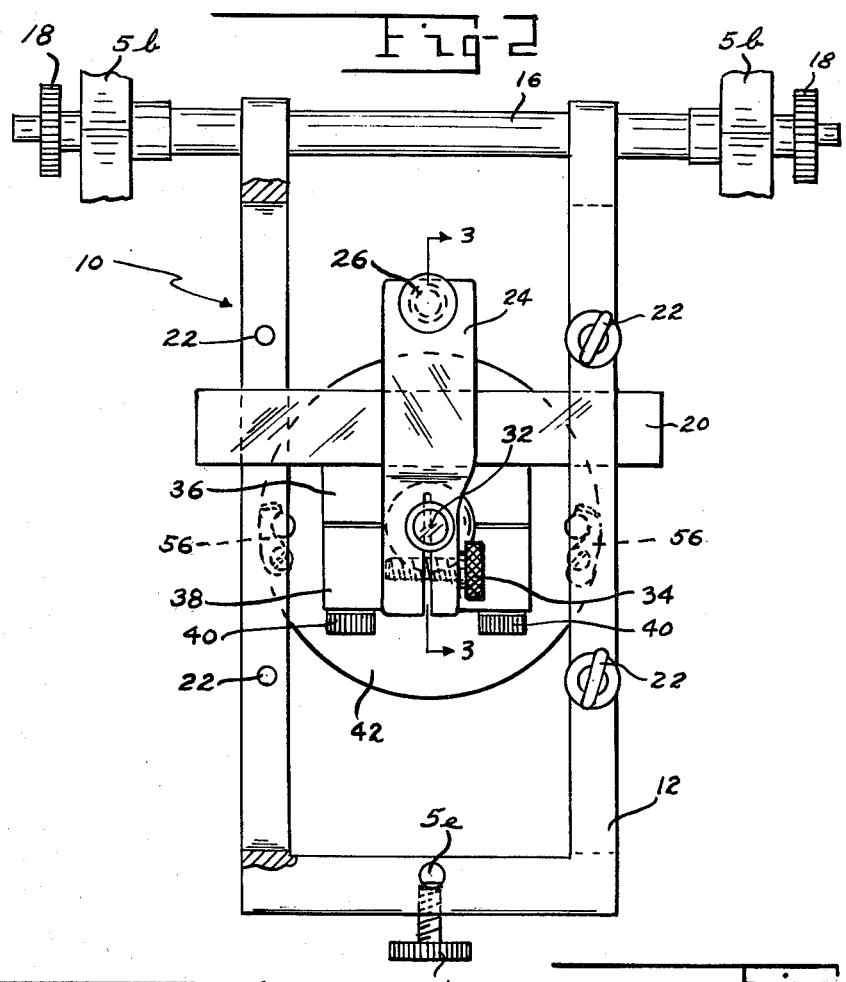
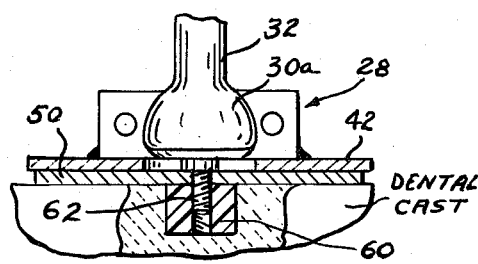
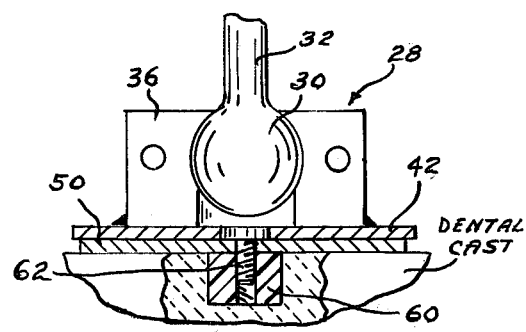
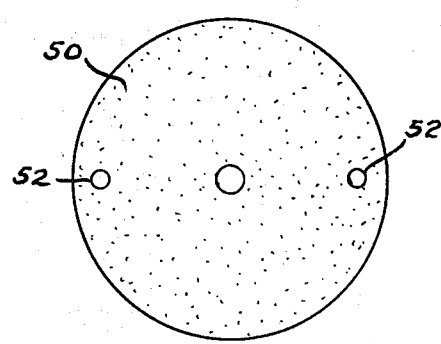
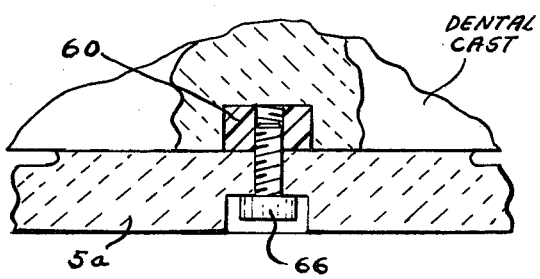

DENTAL ARTICULATOR FOR MOUNTING CASTS WITHOUT PLASTER

REFERENCE TO RELATED U.S. PATENT

U.S. Pat. No. 3,975,489 Cast Ejector, relating to a method of embedding a threaded plastic button into the base of a dental cast.

REFERENCE TO RELATED U.S. PATENT APPLICATION

Ser. No. 788,236 Apparatus and Method For Mounting Dental Casts, filed Apr. 18, 1977, and relating to a prior design of dental articulator for mounting dental casts having threaded apertures.

BACKGROUND OF THE INVENTION

Dental articulators are a common and necessary apparatus in the fabrication of a dental prosthesis. Stripped to its bare essentials, the process of fabricating a prosthesis commences when the dentist takes impressions of the patient's maxillary and mandibular arches which may or may not include natural teeth. These impressions are negative imprints of the arches and become the molds into which the raw material for forming positive dental casts is poured. These positive casts are duplicates of the patient's arches (with or without teeth) and become the primary model to which the prosthesis is to be constructed.

In order to construct an acceptable prosthesis, these dental casts are normally mounted in a dental articulator in order that the maxillary and mandibular casts are maintained in the same anatomical relationship as in the mouth of the patient. This is true in all cases even those where only one prosthesis, as for example the maxillary arch is to be constucted, since the prosthesis must also conform with the relating surfaces on the mandibular arch in the patient's mouth.

Another reason why the dental casts are mounted in the articulator is to permit arrangement of the denture (false) teeth in their proper position for occlusion. On partial dentures, the occlusion of the denture teeth must be with natural teeth. On full dentures greater liberty is often taken to improve function and asthetics. The desired occlusion not only includes the vertical bite but also a degree of lateral movement as well as posterior and anterior movement of the lower jaw. These various movements are produced by the temporomandibular joint which is the joint formed by the condyle of the mandible and the temporal bone. Many dental articulators are built to simulate these movements to a high degree.

Past practice for countless years has been to mount the dental casts in the articulator by means of plaster which is usually a gypsum material. This locates the dental casts in a fixed position. Mounting the dental casts by means of plaster is relatively expensive, is dusty and time consuming because the powdered raw material must be thoroughly mixed with a liquid and the plaster must be allowed to set, the process is subject to error which cannot be compensated, and all utensiles must be thoroughly cleaned after each use. Even in cases where the dental casts have been provided with grooves to facilitate removal and remounting which is often a requirement in the fabricating process, it is very questionable at best whether or not the casts were remounted to their precise originally mounted positions.

At least 95% of all dental articulators built to date have been built for use with plaster mounting techniques. A few have been built which use mechanical mounting devices such as claws or other clamping devices in an attempt to find a better mounting technique than by the use of plaster. These alternate mounting techniques have been far less satisfactory than plaster, especially in those situations where the dental casts are to be removed and remounted to their original positions.

As will be shown, the new apparatus and mounting techniques of the present invention introduce an entirely new concept for the mounting of dental casts which is cheaper, faster and more accurate than prior methods.

SUMMARY OF THE INVENTION

The dental articulator disclosed in U.S. Patent application Ser. No. 788,236, filed Apr. 18, 1977, was one in which the various independent movements could be calibrated to permit the remounting of dental casts to their originally mounted position at any subsequent date by resetting the calibration numbers. Such an articulator is especially useful in situations where it is desired to use a specific articulator on several pairs of dental casts at the same time. Such an articulator is also especially valuable in situations where it is desired to use a face bow.

The present design of articulator is a simplified design which has fewer operating parts of very rugged construction, and is one on which individual parts may be easily replaced if this should become necessary. Whereas the articulator of Ser. No. 788,236 makes provision for moving the lower dental cast after it is mounted in the articulator, the present articulator contemplates mounting the lower dental cast in a fixed position and making all anatomical adjustments to the upper dental cast.

The bulk of the prosthesis built in dental laboratories are built on the simple and less expensive "straight-line" articulators to which the present less expensive design is adaptable. The present design does permit the removal and remounting of dental casts to their original position providing the adjustments are not disturbed. In much of the work performed on straight line articulators, a given set of dental casts remains mounted in the articulator until all work has been completed. The anatomical movements applied to the upper dental cast in the present articulator are identical with the anatomical movements applied to the upper dental cast by the design of Ser. No. 788,236; the novelty of the present articulator being in the specific mechanism for generating the movements and retaining the desired positions. Although the present design is primarily intended for use on a straight-line articulator, the design is equally adaptable for use on the more expensive semi and fully adjustable articulators.

U.S. Pat. No. 3,975,486 Cast Ejector, disclosed a method of embedding a pre-formed button into the base of a dental cast at the time the cast is formed. Ser. No. 788,236 disclosed a method of embedding a threaded button into a hardened dental cast by use of a pour technique. The present invention will disclose a unique method of embedding a pre-formed button into a hardened dental cast.

BRIEF DESCRIPTION OF THE DRAWINGS

FIG. 2 is a plan view of the upper mounting jig;

FIG. 4 is a vertical section taken along the line 4—4 of FIG. 1 and showing details of one form of wobble plate assembly and the manner of securing and supporting a dental cast;

FIG. 5 is a vertical section similar to FIG. 4 and showing details of a second form of wobble plate assembly and the manner of securing and supporting a dental cast;

FIG. 8 is a plan view taken along line 8—8 of FIG. 1 and showing an applied grit surface on a dental cast plate; and, FIG. 9 is a broken section through the central portion of the horizontal base of the articulator body and showing an alternate method of mounting a lower dental cast directly to the articulator body.

DESCRIPTION OF THE PREFERRED EMBODIMENT

At the onset it should be noted that the lower mounting jig may or may not be provided with rotational movement, and with or without vertical movement; and that the upper mounting jig is provided with anterior-posterior movement, with lateral movement, with vertical movement, with rotational movement, and with canting movement by means of a wobble plate.

Figure 1:
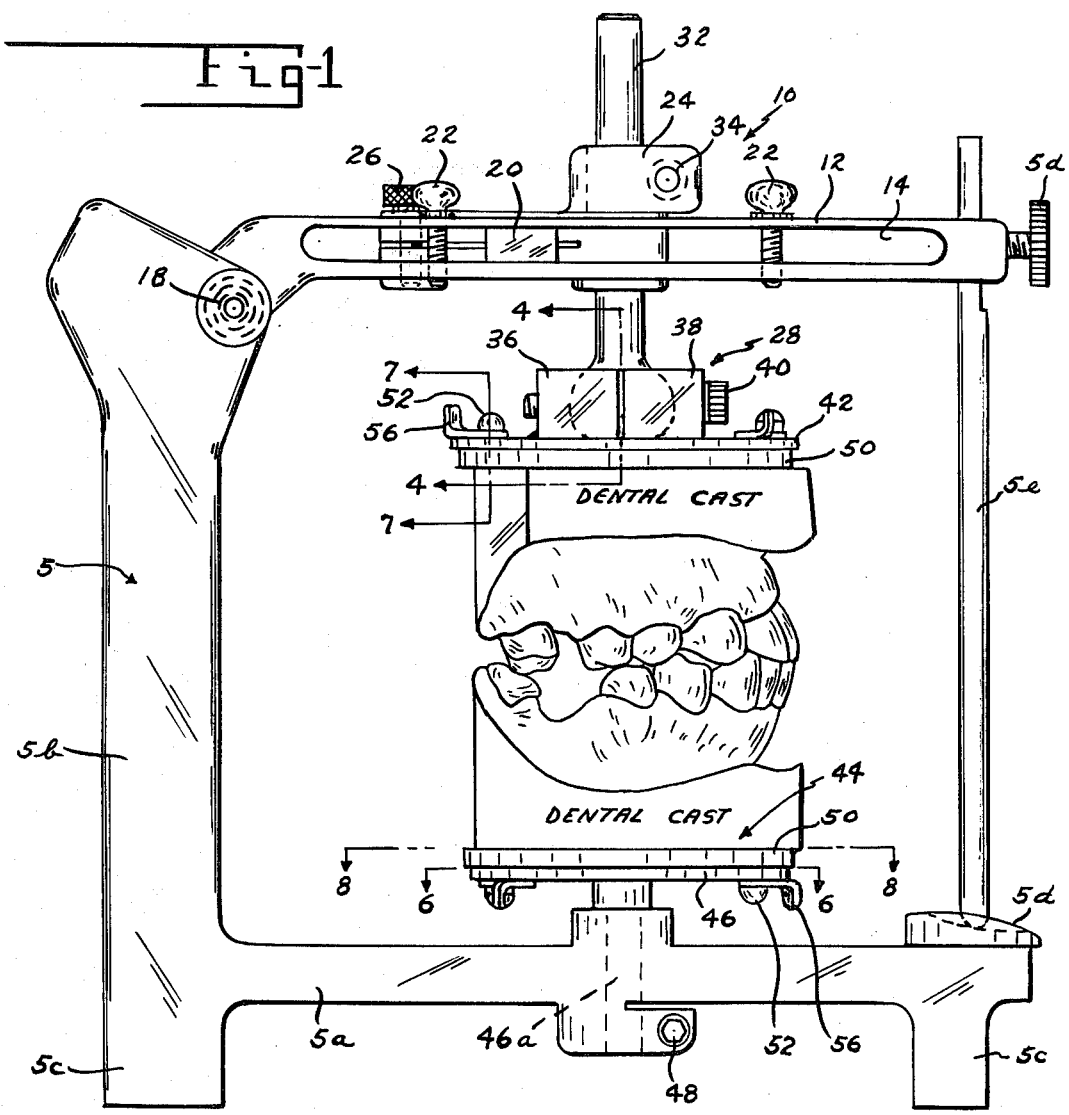
FIG. 1 is a side elevation of a dental articulator supporting an upper and a lower mounting jig to which a matched set of stone dental casts are attached and held in their occlusion position.

Specific reference is made to FIGS. 1 and 2 which depict an upper and a lower dental cast mounting jig joined to a suitable articulator body to form a composite dental articulator for the mounting and adjusting of a matched set of dental casts in their correct anatomical or occlusion position in relationship with each other.

The articulator body 5 has a horizontal base 5a, two vertical upright members 5b, a plurality of suitable feet 5c providing clearance for portions of the lower mounting jig which extend below the base, and an incisal table 5d.

The usual pivoted upper leaf of the conventional dental articulator is replaced by an upper dental cast mounting jig 10 in accordance with the present invention. As indicated, the rear portion of the mounting jig is pivotally joined to the upper portion of the vertical upright members 5b of the articulator body and has a normally horizontal position superimposed over base 5a.

The usual adjustable incisal pin 5e is adjustably retained by the upper mounting jig 10 where it is retained by screw 5d. The functions and use of the incisal pin and incisal table are well known in the dental art and will not be explained.

The upper dental cast mounting jig 10 has a U-shaped frame member 12 having two side elements containing elongated slots 14. The open end of the frame member 12 is joined to a shaft 16, which in turn is pivotally supported by the vertical upright members 5b of the articulator body, and held in place by retaining nuts 18.

A transverse bar member 20 is slidably supported within the elongated slots 14 of frame member 12. The transverse bar member 20 is free to slide fore and aft within the slots and thereby establishes the anterior-posterior position of the upper dental cast in relationship with the lower dental cast. The bar member 20 is retained in its proper adjusted position by tightening screws 22. If desired, suitable stops (not shown) which are well known to the mechanical arts, may be provided to prevent the transverse bar member from laterally sliding out of the frame member. If desired, and within the scope of the present invention, other arrangements may be used for supporting and adjusting the position of the transverse bar in relationship with the frame member.

Figure 3:
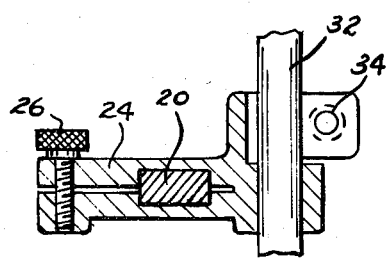
FIG. 3 is a vertical section taken along the line 3—3 of FIG. 2 and showing details of the lateral movement block.

A lateral movememt block member 24 is slidably supported by the transverse bar member 20 as shown in FIGS. 1–3. The lateral movement block member is free to slide to the proper lateral occlusion position of the dental casts, in which position it may be retained by tightening screw 26.

A wobble plate assembly 28, as best shown in FIGS. 1, 4 and 5, is slidably and rotatably retained by the lateral movement block 24. Referring specifically to FIG. 5, a ball 30, having an upward extending stem 32 is slidably retained in a bore of lateral movement block 24 as best shown in FIG. 3. Within the scope of the present invention, the stem 32 may be threaded for engaging a threaded bore in the lateral movement block. A split clamp may be made integral with the lateral movement block 24 as also shown in FIG. 3. The vertical position of stem 32 in relationship with the lateral movement block 24 controls the vertical adjustment of the upper dental cast in relationship with the lower dental cast. The adjusted position may be retained by tightening screw 34.

Again referring specifically to FIG. 5, the ball 30 is surrounded by a vertically split socket comprising a fixed socket half 36 and a movable socket half 38. The two socket halves are retained in their relative position and are tightened against the ball 30 by means of screws 40 which pass through movable socket half 38 and engage threads in the fixed socket half 36.

The fixed socket half 36 is joined to the upper face of wobble plate 42. The fixed socket half may be joined to the wobble plate by brazing or welding as indicated, or, it may be joined by means of screws, rivits, or other means well known to the mechanical arts. The movable socket half 38 slides on top of the wobble plate and is free to slide when one or both of the screws 40 are slightly loosened. Rotational movement of the upper dental cast may be attained by movement about ball 30, or, by rotational movement of stem 32 in the lateral movement block 24; or, by movement at both places. The wobble plate 42 is preferably made in a circular form as shown in FIG. 2.

The lower dental cast mounting jig 44 has a horizontal platform 46 which is preferably of the same circular size and of the same thickness as wobble plate 42 on the upper mounting jig for reasons which will be explained below. The horizontal platform 46 has a circular elongated stem as indicated by 46a in FIG. 1; the stem passing through a bore in base 5a of the articulator body. The lower mounting jig 44 may be rotated to any desired position and retained by tightening screw 48 which engages a split clamp such as is also used on the lateral movement block. In addition to rotational movement, the lower mounting jig 44 is capable of vertical movement if desired. Within the scope of the present invention, the stem 46a may be threaded for engaging a threaded bore in the base of the articulator body.

Superimposed and in face-to-face contact with the horizontal platform is a dental cast plate 50 which is preferably of the same circular shape and size as the wobble plate 42 on the upper mounting jig 10 and the horizontal platform 46 on the lower mounting jig 44. Since, as will be shown, a dental cast plate 50 may be used interchangeably on both the upper and the lower mounting jigs, the dental cast plate on both mounting jigs will be identified by the numeral 50.

Figure 7:
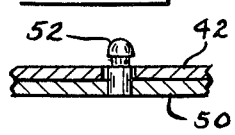
FIG. 7 is a partial vertical section taken along line 7—7 of FIG. 1 and showing a typical latch pin.

The dental cast plates 50 are each provided with two latch pins 52 as best shown on FIG. 7. The latch pins are rigidly joined to the dental cast plates by brazing or by other convenient means. As shown on FIG. 7, the latch pins pass through comparable apertures in the wobble plate (or in the horizontal platform 46 having apertures 54). When in mounted position, the dental cast plates 50 are retained in position by latches 56 which in FIG. 1 are shown mounted to the upper face of wobble plate 42 and to the lower face of horizontal platform 46.

Figure 6:
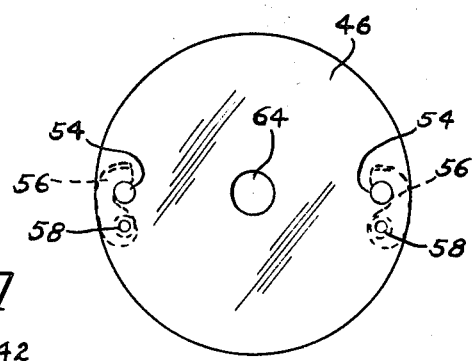
FIG. 6 is a plan view taken along the line 6—6 of FIG. 1 and showing the rotating platform of the lower mounting jig.

FIG. 6 depicts the latches 56 as swing latches which are pivotally supported by pins 58. Other forms of latches may be used, as for example, a latch device in which both latches are operated simultaneously with one operating lever. By using common dimensions on both the wobble plate 42 and the horizontal platform 46, the same dental cast plates 50 may be used on both the upper and the lower mounting jigs.

Reference is now specifically made to FIG. 4 which depicts an alternate design of wobble plate assembly, and which is the design depicted in FIG. 1. The wobble plate 42 and the dental cast plate 50 are identical in both FIG. 4 and FIG. 5. The principal difference is in the ball. Whereas in FIG. 5 a full ball 30 was used, in FIG. 4 a portion of the ball 30a was removed in order to reduce vertical height of the assembly. If somewhat less than half of the ball is removed as indicated, the ball joint has been found to work satisfactorily. Since a portion of the ball was removed, the height of the socket halves was reduced a comparable amount.

Reference is made to U.S. Pat. No. 3,975,489 which teaches a method of embedding a threaded plastic button in a dental cast at the time the dental cast is formed. Further experiments on various methods of forming and embedding buttons in dental casts have produced several variations which are advantageous under certain conditions. It was found that the buttons need not be tapered if they are provided with a surface configuration around their circumference which will prevent the embedded buttons from turning in the dental cast and which will also prevent the buttons from being pulled from the cast. A diamond knurl on the circumference was found to work very well. Another configuration which works very well is to have longitudinal flutes on the circumference to prevent the button from rotating in the dental cast, while at the same time providing the button with one or more circumferential grooves which will prevent the button from pulling out of the cast. It was also found that the knurl or other configuration which may be used can be quite shallow and still have ample retention ability. This non-tapered configuration facilitates the rapid and economical manufacture of buttons on automatic screw machines from plastic bar stock. If fluted bar stock is used, it is only necessary to machine the circumferential grooves.

It was further found that the buttons can be tapped all the way through. Over two years of experimenting with buttons as to configuration, size, and methods of embedding them in dental casts under actual dental laboratory use, both while such dental casts are being formed, and embedding buttons into hardened dental casts, has resulted in certain conclusions. Since some dental casts (especially upper casts) are often rather thin and caution must be used to avoid breaking through the palate portion of the cast, it was found that the buttons should be no longer than one-quarter of an inch, and that seven-sixteenths of an inch is a convenient diameter. Various sizes of threads were tried with the conclusion that the threaded aperture in the button preferably be size 10–32, which size permits good holding power of the dental cast against the mounting plate of the articulator without danger of stripping the plastic thread in the button.

When the above described plastic buttons are embedded in dental casts in accordance with U.S. Pat. No. 3,975,489 the screw in plate 34 as described in column 6, lines 48–54 thereof should extend one-quarter inch from the plate. When the button is screwed into position on the plate, the extending screw will occupy the full thread in the button and will thus prevent any plaster from entering the thread in the button.

It was also found that the above described buttons could be easily and quickly embedded in fully hardened dental casts. A cavity may be drilled into the base of the dental cast by using a one-half inch diameter twist drill ground nearly flat at the end. The cavity should be of such depth that the embedded button will be flush with the base of the dental cast. If desired, a drill stop may be used.

To embed the button, a small amount of plaster is mixed with "slurry water" and some of the mixture is placed into the drilled cavity. The button is placed onto a screw to prevent the fresh unhardened plaster from entering the threaded aperture in the button. There are other methods for keeping fresh plaster out of the screw threads, as for example, by covering the inner end of the button with a waterproof patch adhered in place. Ordinary scotch tape is very good for this purpose.

The button is then pushed into the cavity and the surplus plaster is wiped from the base of the dental cast to prevent hardening on the cast. In the example which has been described, it is noted that the cavity is only one-sixteenth larger in diameter than the diameter of the button. The small amount of fresh plaster filling the void between the button and the cavity wall will set quite fast. It was found that plaster which is mixed with "slurry water" will set faster than plaster which is mixed with fresh water. It was also found that by using the sizes stated, there is no problem in embedding the buttons to be square with the base of the dental casts.

Reference is again made to FIG. 4 which is typical of the manner in which dental casts are mounted to both the upper and the lower mounting jigs. Embedded button 60 is engaged by screw 62 which holds the dental cast against the dental cast plate 50. As shown in both FIG. 4 and FIG. 5, the wobble plate 42 is provided with adequate clearance for the head of screw 62. As shown in FIG. 6, clearance for the screw head on the lower mounting jig is provided with a suitable cavity 64.

Reference is now made to FIG. 8 which shows the face adjacent to the dental cast of a typical dental cast plate 50. This face is covered by a piece of silicon carbide (Carborundum) paper which is adhered in place, or, it may be coated with a suitable adhesive which is sprinkled with a grit material, such as silicon carbide, before the adhesive has hardened. By using such a grit surface, the screw 62 requires a surprisingly small amount of torque to prevent being able to turn the dental cast on the dental cast plate. In spite of its tremendous holding ability, the grit does not leave impressions in the dental cast.

Reference is now made to FIG. 9 which depicts a lower dental cast mounting jig for mounting a lower dental cast directly to the base element of an articulator body. As depicted, the base has a machined pad of substantially the same diameter as a dental cast plate 50; however if desired, the pad may be omitted and the dental cast mounted on an appropriate flat surface. The upper machined surface may have an applied grit surface as described above, if desired. A mounting screw 66 holds the dental cast in its selected position. The head of the screw 66 is shown in a counterbore. If desired, the screw 66 may be retained (kept from falling out) within the base of the articulator by means which are well known in the mechanical arts. If desired, the dental cast plates 50 may be made thicker than shown to provide the screw 62 with like retention means.

It is to be understood that the embodiments of the present invention as shown and described is to be regarded merely as illustrative, and that the invention is susceptible to variations, modifications and changes, without regard to construction methods, within the scope of the appended claims.

We claim:

1. A dental articulator for mounting and supporting a matched upper and a lower dental cast having a threaded aperture in the base of said dental casts, said articulator comprising:
    (a) an articulator body having a base element and at least one vertical element extending upward from said base element;
    (b) a lower dental cast mounting jig supported by the base element of said articulator body; said lower dental cast mounting jig having a screw member extending upward for threadably engaging the threaded aperture in the base of said lower dental cast and retaining it in fixed relationship with the base element of said articulator body; and,
    (c) an upper dental cast mounting jig for mounting and adjusting said upper dental cast in centric anatomical relationship with said lower dental cast; said upper mounting jig having a normally horizontal frame member with spaced apart elongated side elements and being pivotally joined to the vertical element of said articulator body to be superimposed with the base element of said articulator body; an elongated transverse bar member spanning said side elements of said frame member and being retainably slidable fore and aft with the side elements of said frame member for providing anterior-posterior movement of said upper dental cast in relationship with said lower dental cast; a lateral movement block member longitudinally and retainably slidable on said transverse bar member for providing lateral movement of said upper dental cast in relationship with said lower dental cast, and having a vertical bore therethrough spaced to be adjacent and substantially perpendicular to said transverse bar member; a vertical movement member retainably movable in the vertical bore of said lateral movement block member for providing vertical movement of said upper dental cast in relationship with said lower dental cast; a dependent wobble plate assembly operably attached to said vertical movement member for providing retainable rotational and retainable canting movement of said upper dental cast in relationship with said lower dental cast; and, a dental cast mounting plate detachably joined to said wobble plate and carrying a downward extending screw element for threadably engaging the threaded aperture in the base of said upper dental cast and retaining it in fixed relationship with said dental cast mounting plate.

2. A dental articulator for mounting and supporting a matched upper and a lower dental cast having a threaded aperture in the base of said dental casts, said articulator comprising:
    (a) an articulator body having a base element and at least one vertical element extending upward from said base element;
    (b) a lower dental cast mounting jig supported by the base element of said articulator body; said lower dental cast mounting jig having a screw member extending upward for threadably engaging the threaded aperture in the base of said lower dental cast and retaining it in fixed relationship with the base element of said articulator body, the surface on said base element proximate to said lower dental cast being provided with a grit surface; and,
    (c) an upper dental cast mounting jig for mounting and adjusting said upper dental cast in centric anatomical relationship with said lower dental cast; said upper mounting jig having a normally horizontal frame member pivotally joined to the vertical element of said articulator body to be superimposed with the base element of said articulator body; a transverse bar member retainably slidable on said frame member for providing anterior-posterior movement of said upper dental cast in relationship with said lower dental cast; a lateral movement block member retainably slidable on said transverse bar member for providing lateral movement of said upper dental cast in relationship with said lower dental cast; a vertical movement member retainably movable in said lateral movement block member for providing vertical movement of said upper dental cast in relationship with said lower dental cast; a wobble plate assembly operably attached to said vertical movement member for providing retainable rotational and retainable canting movement of said upper dental cast in relationship with said lower dental cast; and, a dental cast mounting plate detachably joined to said wobble plate and carrying a downward extending screw element for threadably engaging the threaded aperture in the base of said upper dental cast and retaining it in fixed relationship with said dental cast mounting plate.

3. A dental articulator for mounting and supporting a matched upper and a lower dental cast having a threaded aperture in the base of said dental casts, said articulator comprising:
    (a) an articulator body having a base element and at least one vertical element extending upward from said base element;

(b) a lower dental cast mounting jig supported by the base element of said articulator body; said lower dental cast mounting jig having a screw member extending upward for threadably engaging the threaded aperture in the base of said lower dental cast and retaining it in fixed relationship with the base element of said articulator body; and, (c) an upper dental cast mounting jig for mounting and adjusting said upper dental cast in centric anatomical relationship with said lower dental cast; said upper mounting jig having a normally horizontal frame member pivotally joined to the vertical element of said articulator body to be superimposed with the base element of said articulator body; a transverse bar member retainably slidable on said frame member for providing anterior-posterior movement of said upper dental cast in relationship with said lower dental cast; a lateral movement block member retainably slidable on said transverse bar member for providing lateral movement of said upper dental cast in relationship with said lower dental cast; a vertical movement member retainably movable in said lateral movement block member for providing vertical movement of said upper dental cast in relationship with said lower dental cast; a wobble plate assembly operably attached to said vertical movement member for providing retainable rotational and retainable canting movement of said upper dental cast in relationship with said lower dental cast; and, a dental cast mounting plate detachably joined to said wobble plate and carrying a downward extending screw element for threadably engaging the threaded aperture in the base of said upper dental cast and retaining it in fixed relationship with said dental cast mounting plate, the face on said dental cast mounting plate proximate to said mounted upper dental cast being provided with a grit surface.

4. A dental articulator for mounting and supporting a matched upper and a lower dental cast having a threaded aperture in the base of said dental casts, said articulator comprising:

(a) an articulator body having a base element and at least one vertical element extending upward from said base element;

(b) a lower dental cast mounting jig supported by the base element of said articulator body; said lower dental cast mounting jig having a screw member extending upward for threadably engaging the threaded aperture in the base of said lower dental cast and retaining it in fixed relationship with the base element of said articulator body, the surface on said base element proximate to said lower dental cast being provided with a grit surface; and, (c) an upper dental cast mounting jig for mounting and adjusting said upper dental cast in centric anatomical relationship with said lower dental cast; said upper mounting jig having a normally horizontal frame member pivotally joined to the vertical element of said articulator body to be superimposed with the base element of said articulator body; a transverse bar member retainably slidable on said frame member movement providing anterior-posterior movement of said upper dental cast in relationship with said lower dental cast; a lateral movement block member retainably slidable on said transverse bar member for providing lateral movement of said upper dental cast in relationship with said lower dental cast; a vertical movement member retainably movable in said lateral movement block member for providing vertical movement of said upper dental cast in relationship with said lower dental cast; a wobble plate assembly operably attached to said vertical movement member for providing retainable rotational and retainable canting movement of said upper dental cast in relationship with said lower dental cast; and, a dental cast mounting plate detachably joined to said wobble plate and carrying a downward extending screw element for threadably engaging the threaded aperture in the base of said upper dental cast and retaining it in fixed relationship with said dental cast mounting plate, the face on said dental cast mounting plate proximate to said mounted upper dental cast being provided with a grit surface.

5. A dental articulator for mounting and supporting a matched upper and a lower dental cast having a threaded aperture in the base of said dental casts, said dental articulator comprising:

(a) an articulator body having a base element and at least one vertical element extending upward from said base element;

(b) a lower dental cast mounting jig for mounting and rotating said lower dental cast to a selected position in relationship with the base element of said articulator body; said lower dental cast mounting jig having a horizontal platform above the base element of said articulator body and being retainably rotatable in the base element of said articulator body; and a dental cast mounting plate detachably joined to said horizontal platform and carrying an upward extending screw element for threadably engaging the threaded aperture in the base of said lower dental cast and retaining it in fixed relationship with said dental cast mounting plate; and, (c) an upper dental cast mounting jig for mounting and adjusting said upper dental cast in centric anatomical relationship with said lower dental cast; said upper mounting jig having a normally horizontal frame member with spaced apart elongated side elements and being pivotally joined to the vertical element of said articulator body to be superimposed with the base element of said articulator body; an elongated transverse bar member spanning said side elements of said frame member and being retainably slidable fore and aft with the side elements of said frame member for providing anterior-posterior movement of said upper dental cast in relationship with said lower dental cast; a lateral movement block member longitudinally and retainably slidable on said transverse bar member for providing lateral movement of said upper dental cast in relationship with said lower dental cast, and having a vertical bore therethrough spaced to be adjacent and substantially perpendicular to said transverse bar member; a vertical movement member retainably movable in the vertical bore of said lateral movement block member for providing vertical movement of said upper dental cast in relationship with said lower dental cast; a dependent wobble plate assembly operably attached to said vertical movement member for providing retainable rotational and retainable canting movement of said upper dental cast in relationship with said lower dental cast; and, a dental cast mounting plate detachably joined to said wobble plate and carrying a downward extending screw element for threadably engaging the threaded aperture in the base of said upper dental cast and retaining it in fixed relationship with said dental cast mounting plate.

6. A dental articulator for mounting and supporting a matched upper and a lower dental cast having a threaded aperture in the base of said dental casts, said dental articulator comprising:

(a) an articulator body having a base element and at least one vertical element extending upward from said base element;

(b) a lower dental cast mounting jig for mounting and rotating said lower dental cast to a selected position in relationship with the base element of said articulator body; said lower dental cast mounting jig having a horizontal platform above the base element of said articulator body and being retainably rotatable in the base element of said articulator body; and a dental cast mounting plate detachably joined to said horizontal platform and carrying an upward extending screw element for threadably engaging the threaded aperture in the base of said lower dental cast and retaining it in fixed relationship with said dental cast mounting plate, the face of said dental cast mounting plate proximate to said mounted lower dental cast being provided with a grit surface; and, (c) an upper dental cast mounting jig for mounting and adjusting said upper dental cast in centric anatomical relationship with said lower dental cast; said upper mounting jig having a normally horizontal frame member pivotally joined to the vertical element of said articulator body to be superimposed with the base element of said articulator body; a transverse bar member retainably slidable on said frame member for providing anterior-posterior movement of said upper dental cast in relationship with said lower dental cast; a lateral movement block member retainably slidable on said transverse bar member for providing lateral movement of said upper dental cast in relationship with said lower dental cast; a vertical movement member retainably movable in said lateral movement block member for providing vertical movement of said upper dental cast in relationship with said lower dental cast; a wobble plate assembly operably attached to said vertical movement member for providing retainable rotational and retainable canting movement of said upper dental cast in relationship with said lower dental cast; and, a dental cast mounting plate detachably joined to said wobble plate and carrying a downward extending screw element for threadably engaging the threaded aperture in the base of said upper dental cast and retaining it in fixed relationship with said dental cast mounting plate.

7. A dental articulator for mounting and supporting a matched upper and a lower dental cast having a threaded aperture in the base of said dental casts, said dental articulator comprising:

(a) an articulator body having a base element and at least one vertical element extending upward from said base element;

(b) a lower dental cast mounting jig for mounting and rotating said lower dental cast to a selected position in relationship with the base element of said articulator body; said lower dental cast mounting jig having a horizontal platform above the base element of said articulator body and being retainably rotatable in the base element of said articulator body; and a dental cast mounting plate detachably joined to said horizontal platform and carrying an upward extending screw element for threadably engaging the threaded aperture in the base of said lower dental cast and retaining it in fixed relationship with said dental cast mounting plate; and, (c) an upper dental cast mounting jig for mounting and adjusting said upper dental cast in centric anatomical relationship with said lower dental cast; said upper mounting jig having a normally horizontal frame member pivotally joined to the vertical element of said articulator body to be superimposed with the base element of said articulator body; a transverse bar member retainably slidable on said frame member for providing anterior-posterior movement of said upper dental cast in relationship with said lower dental cast; a lateral movement block member retainably slidable on said transverse bar member for providing lateral movement of said upper dental cast in relationship with said lower dental cast; a vertical movement member retainably movable in said lateral movement block member for providing vertical movement of said upper dental cast in relationship with said lower dental cast; a wobble plate assembly operably attached to said vertical movement member for providing retainable rotational and retainable canting movement of said upper dental cast in relationship with said lower dental cast; and, a dental cast mounting plate detachably joined to said wobble plate and carrying a downward extending screw element for threadably engaging the threaded aperture in the base of said upper dental cast and retaining it in fixed relationship with said dental cast mounting plate, the face of said dental cast mounting plate proximate to said mounted upper dental cast being provided with a grit surface.

8. A dental articulator for mounting and supporting a matched upper and a lower dental cast having a threaded aperture in the base of said dental casts, said articulator comprising:

(a) an articulator body having a base element and at least one vertical element extending upward from said base element;

(b) a lower dental cast mounting jig for mounting and rotating said lower dental cast to a selected position in relationship with the base element of said articulator body; said lower dental cast mounting jig having a horizontal platform above the base element of said articulator body and being retainably rotatable in the base element of said articulator body; and a dental cast mounting plate detachably joined to said horizontal platform and carrying an upward extending screw element for threadably engaging the threaded aperture in the base of said lower dental cast and retaining it in fixed relationship with said dental cast mounting plate, the face of said dental cast mounting plate proximate to said mounted lower dental cast being provided with a grit surface; and, (c) an upper dental cast mounting jig for mounting and adjusting said upper dental cast in centric anatomical relationship with said lower dental cast; said upper mounting jig having a normally horizontal frame member pivotally joined to the vertical element of said articulator body to be superimposed with the base element of said articulator body; a transverse bar member retainably slidable on said frame member for providing anterior-posterior movement of said upper dental cast in relationship with said lower dental cast; a lateral movement block member retainably slidable on said transverse bar member for providing lateral movement of said upper dental cast in relationship with said lower dental cast; a vertical movement member retainably movable in said lateral movement block member for providing vertical movement of said upper dental cast in relationship with said lower dental cast; a wobble plate assembly operably attached to said vertical movement member for providing retainable rotational and retainable canting movement of said upper dental cast in relationship with said lower dental cast; and, a dental cast mounting plate detachably joined to said wobble plate and carrying a downward extending screw element for threadably engaging the threaded aperture in the base of said upper dental cast and retaining it in fixed relationship with said dental cast mounting plate, the face of said dental cast mounting plate proximate to said mounted upper dental cast being provided with a grit surface.

9. A dental cast mounting jig for mounting and adjusting an upper dental cast having a threaded aperture in the base of said upper dental cast and being adapted for joining to an element of a dental articulator having means for supporting a lower dental cast on a base element of said dental articulator, said mounting jig comprising: a normally horizontal frame member with spaced apart elongated side elements and being adapted for joining to an element of said dental articulator to be superimposed with the base element of said articulator; an elongated transverse bar member spanning said side elements of said frame member and being retainably slidable fore and aft with the side elements of said frame member for providing anterior-posterior movement of said upper dental cast in relationship with said lower dental cast; a lateral movement block member longitudinally and retainably slidable on said transverse bar member for providing lateral movement of said upper dental cast in relationship with said lower dental cast, and having a vertical bore therethrough spaced to be adjacent and substantially perpendicular to said transverse bar member; a vertical movement member retainably movable in the vertical bore of said lateral movement block member for providing vertical movement of said upper dental cast in relationship with said lower dental cast; a dependent wobble plate assembly operably attached to said vertical movement member for providing retainable rotational and retainable canting movement of said upper dental cast in relationship with said lower dental cast; and, a dental cast mounting plate detachably joined to said wobble plate assembly and carrying a downward extending screw element for threadably engaging the threaded aperture in the base of said upper dental cast and retaining it in fixed relationship with said dental cast mounting plate.

10. A dental cast mounting jig for mounting and adjusting an upper dental cast having a threaded aperture in the base of said upper dental cast and being adapted for joining to an element of a dental articulator having means for supporting a lower dental cast on a base element of said dental articulator, said mounting jig comprising: a normally horizontal frame member adapted for joining to an element of said dental articulator to be superimposed with the base element of said articulator; a transverse bar member retainably slidable on said frame member for providing anterior-posterior movement of said upper dental cast in relationship with said lower dental cast; a lateral movement block member retainably slidable on said transverse bar member for providing lateral movement of said upper dental cast in relationship with said lower dental cast; a vertical movement member retainably movable in said lateral movement block member for providing vertical movement of said upper dental cast in relationship with said lower dental cast; a wobble plate assembly operably attached to said vertical movement member for providing retainable rotational and retainable canting movement of said upper dental cast in relationship with said lower dental cast; and, a dental cast mounting plate detachably joined to said wobble plate assembly and carrying a downward extending screw element for threadably engaging the threaded aperture in the base of said upper dental cast and retaining it in fixed relationship with said dental cast mounting plate, the face of said dental cast mounting plate proximate to said upper dental cast being provided with a grit surface.

11. A dental articulator in accordance with claim 1 in which the surface on said base element proximate to said mounted lower dental cast is provided with a grit surface.

12. A dental articulator in accordance with claim 1 in which the face on said dental cast mounting plate proximate to said mounted upper dental cast is provided with a grit surface.

13. A dental articulator in accordance with claim 1 in which the surface on said base element proximate to said mounted lower dental cast and the face on said dental cast mounting plate proximate to said mounted upper dental cast are provided with a grit surface.

14. A dental articulator in accordance with claim 1 in which said transverse bar member in said upper mounting jig is retainably slidable in elongated slots in the side elements of said frame member.

15. A dental articulator in accordance with claim 5 in which the face of said dental cast mounting plate proximate to said mounted lower dental cast is provided with a grit surface.

16. A dental articulator in accordance with claim 5 in which the face of said dental cast mounting plate proximate to said mounted upper dental cast is provided with a grit surface.

17. A dental articulator in accordance with claim 5 in which the face of said dental cast mounting plate proximate to said mounted lower dental cast and the face of said dental cast mounting plate proximate to said mounted upper dental cast are provided with a grit surface.

18. A dental articulator in accordance with claim 5 in which said transverse bar member in said upper mounting jig is retainably slidable in elongated slots in the side elements of said frame member.

19. A dental cast mounting jig in accordance with claim 9 in which the face of said dental cast mounting plate proximate to said upper dental cast is provided with a grit surface.

20. A dental cast mounting jig in accordance with claim 9 in which said transverse bar member in said mounting jig is retainably slidable in elongated slots in the side elements of said frame member.

* * * * *